United States Patent [19]

Berg et al.

[11] Patent Number: 5,228,956
[45] Date of Patent: Jul. 20, 1993

[54] SEPARATION OF 3-PENTANONE FROM FORMIC ACID BY EXTRACTIVE DISTILLATION

[75] Inventors: Lloyd Berg, 1314 S. Third Ave., Bozeman, Mont. 59715; Rudolph J. Szabados, Bozeman, Mont.

[73] Assignee: Lloyd Berg, Bozeman, Mont.

[21] Appl. No.: 955,415

[22] Filed: Oct. 2, 1992

[51] Int. Cl.$^5$ .................. B01D 3/40; C07C 45/83; C07C 53/02
[52] U.S. Cl. ........................ 203/51; 203/56; 203/60; 203/61; 203/62; 203/63; 562/609; 568/410
[58] Field of Search ............ 203/62, 51, 60, 61, 203/63, 56; 568/410; 562/609

[56] References Cited

U.S. PATENT DOCUMENTS

| | | | |
|---|---|---|---|
| 2,010,384 | 8/1935 | Van Melsen et al. | 568/410 |
| 2,588,268 | 3/1952 | Mercer et al. | 203/62 |
| 3,013,954 | 12/1961 | Pacoud et al. | 203/62 |
| 3,228,985 | 1/1966 | Carpenter et al. | 568/410 |
| 3,265,592 | 8/1966 | Van Der Weel | 568/410 |
| 3,394,058 | 7/1968 | Hohenschutz | 203/62 |
| 4,793,901 | 12/1988 | Berg et al. | 203/63 |
| 4,840,707 | 6/1989 | Berg et al. | 203/63 |
| 4,859,285 | 8/1989 | Berg et al. | 203/51 |
| 4,948,471 | 8/1990 | Berg et al. | 203/62 |

Primary Examiner—Wilbur Bascomb, Jr.

[57] ABSTRACT

3-Pentanone cannot be completely removed from 3-pentanone and formic acid mixtures by distillation because of the presence of the maximum azeotrope. 3-Pentanone can be readily removed from 3-pentanone-formic acid mixtures by extractive distillation in which the extractive agent is cyclopentanone, either alone or admixed with certain high boiling organic compounds. Examples of effective agents are cyclopentanone; cyclopentanone and 2-methoxyethyl ether; cyclopentanone, adiponitrile and octanoic acid.

2 Claims, No Drawings

SEPARATION OF 3-PENTANONE FROM FORMIC ACID BY EXTRACTIVE DISTILLATION

This application is related to application Ser. No. 07/421,975 filed Oct. 16, 1989, abandoned.

FIELD OF THE INVENTION

This invention relates to a method for separating formic acid from 3-pentanone using certain higher boiling liquids as the agent in extractive distillation.

DESCRIPTION OF PRIOR ART

Extractive distillation is the method of separating close boiling compounds or azeotropes by carrying out the distillation in a multi-plate rectificatior column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Formic acid, B.P.=100.8° C. and 3-pentanone, B.P.=102° C. form a maximum azeotrope boiling at 105.2° C. and containing 33 wt. % formic acid. When these two are found together in mixtures, either alone or with other liquids, distillation will only produce the azeotrope, never pure formic acid or 3-pentanone. Thus any liquid mixture containing these two will on distillation produce the azeotrope. Extractive distillation would be an attractive method of effecting the separation of formic acid from 3-pentanone if agents can be found that (1) will break the formic acid - 3-pentanone azeotrope and (2) are easy to recover from the formic acid, that is, form no azeotrope with formic acid and boil sufficiently above formic acid to make the separation by rectification possible with only a few theoretical plates.

Extractive distillation typically requires the addition of an equal amount to twice as much extractive agent as the 3-pentanone and formic acid on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The objects of this invention are to provide a process or method of extractive distillation that will enhance the relative volatility of 3-pentanone to formic acid in their separation in a rectification column. It is a further object of this invention to identify suitable extractive distillation agents which will eliminate the 3-pentanone-formic acid azeotrope and make possible the production of pure 3-pentanone and formic acid by rectification. It is a further object of this invention to identify organic compounds that are stable, can be separated from formic acid by rectification with relatively few plates and can be recycled to the extractive distillation column and reused with little decomposition.

SUMMARY OF THE INVENTION

The objects of the invention are provided by a process for separating 3-pentanone from formic acid which entails the use of certain oxygen containing organic compounds as the agent in extractive distillation.

DETAILED DESCRIPTION OF THE INVENTION

We have discovered that cyclopentanone, either alone or admixed with other high boiling organic compounds, will effectively negate the 3-pentanone - formic acid maximum azeotrope and permit the separation of 3-pentanone from formic acid by rectification when employed as the agent in extractive distillation. Table 1 lists cyclopentanone and its mixtures and the approximate proportions that we have found to be effective.

TABLE 1

Extractive Distillation Agents Which Are Effective In Breaking The 3-Pentanone - Formic Acid Azeotrope.

| Compounds | Ratios | | Relative Volatility |
|---|---|---|---|
| Cyclopentanone | 1 | | 1.5 |
| Cyclopentanone, Aiponitrile | $(1)^2$ | $(3/5)^2$ | 1.4   1.5 |
| Cyclopentanone, 2-Methoxyethyl ether | " | " | 2.3   2.6 |
| Cyclopentanone, Adiponitrile, Octanoic acid | $(1)^3$ | $(2/5)^3$ | 1.3   1.1 |
| Cyclopentanone, 2-Methoxyethyl ether, Methyl phenyl acetate | " | " | 1.6   2.1 |

The data in Table 1 was obtained in a vapor-liquid equilibrium still. In every case, the starting material was the 3-pentanone - formic acid azeotrope. The ratios are the parts by weight of extractive agent used per part of 3-pentanone - formic acid azeotrope. The relative volatilities are listed for each of the two ratios employed. The compounds which are effective are cyclopentanone when used alone and adiponitrile, 2-methoxyethyl ether, octanoic acid and methyl phenyl acetate when mixed with cyclopentanone.

THE USEFULNESS OF THE INVENTION

The usefulness or utility of this invention can be demonstrated by referring to the data presented in Table 1. All of the successful extractive distillation agents show that 3-pentanone and formic acid can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity 3-pentanone and formic acid from any mixture of these two including the maximum azeotrope. The stability of the compounds used and the boiling point difference is such that complete recovery and recycle is obtainable by a simple distillation and the amount required for make-up is small.

WORKING EXAMPLES

Example 1

Fifty grams of the 3-pentanone - formic acid azeotrope and 50 grams of cyclopentanone were charged to a vapor-liquid equilibrium still and refluxed for seven hours. Analysis indicated a vapor composition of 51.9% 3-pentanone, 48.1% formic acid, a liquid composition of 43.3% 3-pentanone, 56.7% formic acid which is a relative volatility of 1.5.

Example 2

Fifty grams of the 3-pentanone - formic acid azeotrope, 25 grams of cyclopentanone and 25 grams of adiponitrile were charged to the vapor-liquid equilibrium still and refluxed for 3 hours. Analysis indicated a vapor composition of 53.1% 3-pentanone, 46.9% formic acid and a liquid composition of 45.5% 3-pentanone, 54.5% formic acid which is a relative volatility of 1.4. Five grams of cyclopentanone & five grams of adiponitrile were added and refluxing continued for another two hours. Analysis indicated a vapor composition of 56.8% 3-pentanone, 43.2% formic acid and a liquid composition of 47.7% 3-pentanone, 52.3% formic acid which is a relative volatility of 1.5.

We claim:

1. A method for recovering 3-pentanone from a mixture of 3-pentanone and formic acid which comprises distilling a mixture of 3-pentanone and formic acid in a rectification column in the presence of about one part of an extractive agent per part of 3-pentanone - formic acid mixture, recovering 3-pentanone as overhead product and obtaining the formic acid and the extractive agent from the stillpot, wherein said extractive agent consists of cyclopentanone.

2. A method for recovering 3-pentanone from a mixture of 3-pentanone and formic acid which comprises distilling a mixture of 3-pentanone and formic acid in a rectification column in the presence of about one part of an extractive agent per part of 3-pentanone - formic acid mixture, recovering 3-pentanone as overhead product and obtaining the formic acid and the extractive agent from the stillpot, wherein said extractive agent consists of cyclopentanone and a material selected from the group consisting of adiponitrile, 2-methoxyethyl ether, octanoic acid, methyl phenyl acetate and mixtures thereof.

* * * * *